(12) United States Patent
Albert et al.

(10) Patent No.: US 8,003,405 B2
(45) Date of Patent: Aug. 23, 2011

(54) CALIBRATING DISPENSING DEVICE PERFORMANCE FOR COMPLEX AND/OR NON-AQUEOUS LIQUIDS

(75) Inventors: Keith J. Albert, Auburn, ME (US); John Thomas Bradshaw, Gorham, ME (US); Alex L. Rogers, Gray, ME (US)

(73) Assignee: Artel, Inc., Westbrook, ME (US)

( * ) Notice: Subject to any disclaimer, the term of this patent is extended or adjusted under 35 U.S.C. 154(b) by 1533 days.

(21) Appl. No.: 11/305,301

(22) Filed: Dec. 16, 2005

(65) Prior Publication Data
US 2007/0141709 A1 Jun. 21, 2007

(51) Int. Cl.
*G01B 11/22* (2006.01)
(52) U.S. Cl. ........ 436/174; 436/164; 436/166; 436/179; 422/68.1; 422/82.05; 422/82.09
(58) Field of Classification Search .............. 422/55–57, 422/68.1, 82.05–82.08, 82.09, 82.11; 73/1.73, 73/149, 861, 861.04, 861.07; 356/627, 408, 356/409, 425; 436/164, 166, 174, 179
See application file for complete search history.

(56) References Cited

U.S. PATENT DOCUMENTS

| | | | |
|---|---|---|---|
| 3,492,095 A | 1/1970 | Tillem | |
| 3,565,537 A | 2/1971 | Fielding | |
| 3,705,000 A | 12/1972 | Guerra | |
| 3,737,237 A | 6/1973 | Zurasky | |
| 3,869,211 A | 3/1975 | Watanabe et al. | |
| 3,920,580 A | 11/1975 | Mast | |
| 4,128,339 A | 12/1978 | Yamazaki et al. | |
| 4,248,536 A | 2/1981 | Hijikata | |
| 4,305,659 A | 12/1981 | Bilstad et al. | |
| 4,354,376 A | 10/1982 | Greenfield et al. | |
| 4,357,105 A | 11/1982 | Liretz | |

(Continued)

FOREIGN PATENT DOCUMENTS
EP 0431578 B1 6/1991

OTHER PUBLICATIONS

Bradshaw et al. "Improving Automated Liquid Handler Performance Through Reliable Volume Delivery Measurements" PittCon Poster, Presented Feb. 27 thru Mar. 4, 2005, Orlando, Florida, USA.*

(Continued)

*Primary Examiner* — Jill Warden
*Assistant Examiner* — Cedric Chan
(74) *Attorney, Agent, or Firm* — Verrill Dana, LLP; Chris A. Caseiro

(57) ABSTRACT

A method for determining the volume of a test liquid aliquot used to calibrate a liquid delivery device. The method is useful for determining the volume of an aliquot of a test liquid which is complex, non-aqueous or both. A mixture contains the test liquid and a stock solution including a first dye, the first dye having absorbance characteristics which are measurably distinguishable from the absorbance characteristics of a second dye. The mixture is mixed with a diluent including the second dye to form a sample solution used to measure absorbances of the first dye and the second dye. The test liquid and the stock solution are combined gravimetrically in a controlled ratio so that the flow characteristics of the test-stock mixture correspond to the flow characteristics of the test liquid and without affecting the ability to distinguish the absorbance characteristics between the first dye and the second dye.

12 Claims, 6 Drawing Sheets

U.S. PATENT DOCUMENTS

| | | | |
|---|---|---|---|
| 4,405,235 | A | 9/1983 | Rossiter |
| 4,582,684 | A | 4/1986 | Vogel et al. |
| 4,595,561 | A | 6/1986 | Thornton et al. |
| 4,797,000 | A | 1/1989 | Curtis |
| 4,805,623 | A | 2/1989 | Jobsis |
| 5,064,282 | A | 11/1991 | Curtis |
| 5,092,677 | A | 3/1992 | Curtis |
| 5,125,747 | A | 6/1992 | Sayegh et al. |
| 5,244,813 | A | 9/1993 | Walt et al. |
| 5,247,345 | A | 9/1993 | Curtis |
| 5,258,308 | A | 11/1993 | Freeman et al. |
| 5,298,978 | A | 3/1994 | Curtis et al. |
| 5,492,673 | A | 2/1996 | Curtis et al. |
| 5,766,875 | A | 6/1998 | Hafeman et al. |
| 5,959,738 | A | 9/1999 | Hafeman et al. |
| 5,963,318 | A | 10/1999 | Held |
| 6,188,476 | B1 | 2/2001 | Hafeman et al. |
| 6,320,662 | B1 | 11/2001 | Hafeman et al. |
| 6,339,472 | B1 | 1/2002 | Hafeman et al. |
| 6,741,365 | B2 * | 5/2004 | Curtis ........................... 356/627 |
| 2002/0149772 | A1 | 10/2002 | Halg |
| 2004/0246501 | A1 | 12/2004 | Curtis |
| 2005/0168737 | A1 | 8/2005 | Bradshaw et al. |

OTHER PUBLICATIONS

Knaide et al. "A Two-Dye Photometric System for Calibration of Multichannel Automated Liquid Handlers" AABB Annual Meeting, Poster, Presented Oct. 15-18, 2005, Seattle, Washington, USA.*

Cohn et al., "Precision Techniques for Measuring Liquid Quantity," Control Engineering, vol. 15, Jan. 1968, U.S., pp. 51-55 (5 pages).

Waring et al., "The Chemistry and Application of Dyes," 1990, Plenum Press, New York, U.S., p. 282 (2 pages).

Lubs, "The Chemistry of Synthetic Dyes and Pigments," Amer. Chem. Soc., Color and Chemical Constitution of Dyes, 1970, Hefner Publishing, Darien, CT, US, pp. 675-676 (3 pgs).

International Standard, ISO 8655-7, "Piston-operated volumetric apparatus—Part 7: Non-gravimetric methods for the assessment of equipment performance," Sep. 1, 2005, (27 pgs).

Taylor et al., "A Standard Operating Procedure for Assessing Liquid Handler Performance in High-Throughput Screening", Journal of Biomolecular Screening 7:554-569 (2002).

Knaide, T. et al., A Two-Dye Photometric System for Calibration of Multichannel Automated Liquid Handlers, AABB presentation, 35 pp., 2003.

Bradshaw, J. T. et al., A Novel Dual Dye Photometric Method for Automated Liquid Handler Verification, AAPS presentation, 40 pp., Oct. 2003.

Bradshaw, J. T., A Multichannel Verification System for Ensuring the Accuracy and Precision of Liquid Delivery, ALA LabAutomation presentation, 37 pp., Feb. 2004.

Bradshaw, J. T. et al., Validation Testing of a New Dual-Dye Photometric Method for Evaluating Multichannel Liquid Delivery Performance, ALA LabFusion presentation, 29 pp., Jun. 2004.

Bradshaw, J. T. et al., Accurate and precise Multichannel Volumetric Verification of Liquid Delivery from Automated Liquid Handlers Using a Novel Dual-Dye Photometric System, ISLAR presentation, 20 pp., Oct. 2003.

Bradshaw, J. T., A Dual-Dye Photometric Method for Verifying the Performance of Multichannel Liquid Handling Equipment, Bay Area LRIG presentation, 39 pp., Feb. 2004.

Bradshaw, J. T. et al., Calibration of Multichannel Liquid Delivery Devices using a New Photometric Method, LRIG presentation, 25 pp., Mar. 2003.

Knaide, T. et al., A Two-Dye Photometric System for Calibration of Multichannel Automated Liquid Handlers, PittCon presentation, 30 pp., 2004.

Rodrigues, G. et al., A Two-Dye Photometric System for Calibration of Multichannel Automated Liquid Handlers, SBS poster, 8 pp., Sep. 2003.

Bradshaw, J. T. et al., Ensuring Performance of Automated Liquid Handlers with the Ariel MVS(TM) Multichannel Verification System, WCBP presentation, 35 pp., Jan. 2004.

Curtis, R., Calibration of Multichannel Liquid Delivery Devices using a New Photometric Method, SBS presentation, 31 pp., Sep. 2002.

Bradshaw, J. T., Development, Testing and Validation of a Dual-Dye Photometric Method for Assessing Automated Liquid Handler Performance, SBS Presentation, 31 pp., Sep. 2004.

A Dual-Dye Photometric Method for Verifying the Performance of Multichannel Liquid Handling Equipment, marketing presentation, 7 pp., Nov. 2003.

A Dual-Dye Photometric Method for Verifying the Performance of Multichannel Liquid Handling Equipment, marketing presentation, 6 pp., Oct. 2003.

A Multichannel Verification System for Ensuring the Accuracy and Precision of Liquid Delivery, marketing presentation, 7 pp., Mar. 2004.

Calibration of Multichannel Liquid Delivery Devices using a New Photometric Method, marketing presentation, 6 pp., Jan. 2003.

The Ariel MVS (TM): A Multichannel Verification System for Testing Liquid Handler Performance, marketing presentation, 5 pp., Aug. 2004.

Calibration of Automated Liquid Handlers Using a Dual Dye Photometric Method, PittCon 2003 abstract, 1 pp., 2003.

Held, P. et al., Performance Verification of Bio-Tek's Precision 2000 (TM) Using Artel's Multichannel Volume Verification (MVV(TM)) System, SBS abstract, 1 pp., 2003.

Bradshaw, J. T. et al, Validation of the Artel MVS (TM) Multichannel Verification System: A New Dual-Dye Method for Testing Automated Liquid Handler Performance, AACC abstract, 1 pp., 2004.

Bradshaw, J. T. et al, Validation of a Dual-Dye Photometric Method for Testing Automated Liquid Handler Performance, AOAC abstract, 1 pp., 2004.

Bradshaw, J. T. et al., A Novel Dual Dye Photometric System for Testing the Volumetric Performance of Multichannel Equipment, LRIG Bay Area abstract, 1 pp., 2003.

* cited by examiner

CALIBRATING DISPENSING DEVICE PERFORMANCE FOR COMPLEX AND/OR NON-AQUEOUS LIQUIDS

BACKGROUND OF THE INVENTION

1. Field of the Invention

The present invention relates to a system for determining the volume of a liquid. More particularly, the present invention relates to volume dispensing systems which dispense varied liquids.

2. Description of the Prior Art

Multichannel volume dispensing devices, such as automated liquid handling (ALH) systems, are widely used in drug discovery assays and other high-throughput screening processes. Multichannel volume dispensing devices are also referred to herein as liquid handlers and as dispensing systems. The performance of these systems is heavily based on the ability to accurately and precisely deliver volumes of specific reagents. For instance, because concentrations of species within an assay are volume-dependent, assay integrity and the subsequent interpretation of assay results are directly tied to the accuracy of the delivered volume, which is ultimately tied to ALH performance. This direct connection between assay results and ALH performance demonstrates an imperative need to ensure proper performance of ALH equipment, especially for critically important assays.

There is, however, much to consider when choosing the best method for calibrating dispensing devices. For one, volumes that must be accurately and precisely delivered are typically small, so the method of calibration selected must be particularly effective for measuring small volumes. Further, it is important that results produced by the method be standardized, or more specifically, traceable to national standards to achieve consistent volumetric delivery performance among all dispensing devices regardless of make, model, manufacturer or location of the device. It is also important that the method be robust, rapid, and easy to use in the laboratory by in-house personnel so that the volumetric performance of the device can be verified frequently and with minimal device downtime. This need to be efficient is especially critical for multichannel device calibration, since for these devices, calibration must be performed not once, but for each channel separately to assure accuracy and precision within the entire device. For purposes of the present invention description, calibration of a device includes verification and/or validation of the device.

Prior methods of determining liquid volume, including those designed to satisfy the aforementioned considerations, are well-documented. Several of these methods, such as gravimetric, fluorometric and photometric approaches, have been used to calibrate liquid handling systems with varying degrees of success. A thorough description of these methods is presented in U.S. Pat. No. 6,741,365 issued to Curtis ("the Curtis '365 Patent"), which is incorporated entirely herein. Although widely used, gravimetric analysis generally does not provide information about individual channel performance for multichannel dispensing devices and is difficult to perform at low volumes. By comparison, a fluorescence approach gives information about each channel and readily extends to low volumes. However, the well-known variability inherent in fluorescent dyes caused by quenching and photobleaching makes an accurate volume determination difficult to achieve. These limitations also make standardization of fluorescence approaches difficult to achieve, and have hindered the development of internationally recognized fluorescence standards. As with fluorescence, a photometric approach provides information about each channel, but more importantly the photometric approach allows for volume measurements which are traceable to national and international standards.

Added to the limitations of these prior methods is the problem that none is particularly well-suited for calibrating liquid handling devices to precisely and accurately dispense any, or all, liquid types. Indeed, the ability of a liquid handler to properly dispense can vary from liquid-to-liquid. While liquid handling instruments are capable of dispensing a wide array of reagent types, it is commonly known that performance parameters can vary significantly between different solvent types (e.g., aqueous, organic, serum, etc.). A dispensing device which precisely and accurately delivers an aqueous-based liquid, water, for example, may not be as precise and as accurate in dispensing an organic-based liquid, dimethyl sulfoxide (DMSO), for example. Thus, a methodology used for aqueous-based samples may dispense a significantly different amount of volume if employed for an organic-based solution of different characteristics. Liquid handler software packages incorporating computational algorithms may provide users with the ability to adjust dispense methodologies to compensate for solvent-dependent performance differences. However, unless an accurate measurement of the liquid handler performance is collected, these parameters could lead to a false-sense of performance when a reagent from a different solvent-type is employed. In particular, prior methods for calibrating delivery devices are not optimally designed for calibrating liquid handlers to dispense liquids which are non-aqueous and/or complex. As discussed herein, the term complex is used to refer to any liquid type (aqueous, organic, etc.) that has one or more components and/or additives, such as dyes, other liquid types, salts, sugars, detergents, surfactants, proteins, bio- or cellular-based materials, chelating agents, inorganic materials, etc.

Therefore, what is needed is a system and related method to precisely and accurately determine the volume of aqueous, complex, non-aqueous, or complex and non-aqueous liquids that are dispensed from a liquid handling device. The system should include one or more of a determination method, an apparatus, and a kit combining an apparatus and instructions for carrying out the method. The system and related method should be suitable for combining a liquid or solution of interest for use in a liquid handler with a liquid or solution including one or more dyes suitable for photometric or other volume measurement techniques.

SUMMARY OF THE INVENTION

The present invention is a method and related system to create a test-stock mixture, which is subsequently dispensed from a liquid handling device, to be used in a volume determination for calibration of the liquid handling device or other devices of interest. This test-stock mixture enables the system to verify the performance of the liquid handler by quantifying the volume of liquid dispensed therefrom. For the purpose of the description of the present invention, a test liquid forming part of the test-stock mixture is primarily a complex and/or non-aqueous liquid, but may also be an aqueous liquid. The test-stock mixture is prepared by mixing the test liquid, such as DMSO, for example, with a stock solution containing a first dye and, optionally, a second dye. The first and second dyes have known absorbance characteristics and are used in a volume determination process useful in the calibration of liquid handling devices. The system includes instructions for mixing the test liquid with the stock solution to form the test-stock mixture in a controlled ratio with a known dilution ratio. The controlled mixture ratio produces a controlled, and therefore known, change in the absorbance per pathlength determined by an accurate determination of the dilution ratio. The flow characteristics of the resulting test-stock mixture correspond to the flow characteristics of the test liquid. In addition, the mix ratio of the test liquid and the stock solution preferably provides such flow characteristics without substantially affecting the ability to distinguish the absorbance characteristics between the first dye and the second dye in a sample solution under test, the sample solution including the test-stock mixture (with either the first dye only or the first and second dye) and a diluent including the second dye.

The mixing of the test liquid and the stock solution is performed gravimetrically so that the mass ratio of test liquid to stock solution is controlled. The ultimate volume ratio of the test liquid to stock solution is thereby based on the density values of all liquids employed to prepare the test-stock mixture. In general, the resultant test-stock mixture does not appreciably change the absorbance characteristics of the dyes in the stock solution (such as by a change in peak absorbance or in the absorbance spectrum, for example). However, if the mixture of the test liquid and the stock solution does result in a change in the absorbance characteristic of either or both of the first dye and the second dye, a correction factor may be calculated and applied to the equations used to determine volume. Whether particular dye absorbance characteristics do or do not change, it is only necessary that the absorbance characteristics of the first dye and the second dye are distinguishable from one another.

The present invention provides a method and related apparatus for precisely and accurately determining the volume of a liquid aliquot of the test-stock mixture. In one embodiment of the apparatus of the present invention, the apparatus is an analytical balance, a liquid holder, a spectrophotometer, and a computing system which may be used to carry out the method of volume determination including the test-stock mixture.

In multiple embodiments of a kit of the present invention, the kit includes the instructions for carrying out the method and one or more stock solutions to make test-stock mixtures, liquid holders, dyes, and computer-executable software used to carry out the method for mixing the test liquid and the stock solution in controlled ratios, and a method for determining volume.

The present invention also includes a method and related system to create a test-diluent mixture, which may be used to make up a volume within a liquid holder including a liquid, such as a test-stock mixture as described above, for example, to be used in a volume calibration determination for a liquid handling device. The test-diluent mixture is prepared by mixing the test liquid with a diluent including the second dye only. The system includes instructions for mixing the test liquid with the diluent to form the test-diluent mixture in a controlled ratio with a known dilution ratio. The controlled mixture ratio produces a controlled, and therefore known, change in the absorbance per pathlength determined by an accurate determination of the dilution ratio. The mix ratio of the test liquid and the diluent preferably does not substantially affect the ability to distinguish the absorbance characteristics between the first dye and the second dye in a sample solution under test, the sample solution including the liquid of interest to be dispensed from a liquid handling device (with either the first dye only or the first and second dye) and the test-diluent mixture.

These and other features and advantages of the invention will be apparent upon review of the following detailed description, appended drawings and accompanying claims.

DETAILED DESCRIPTION OF THE PREFERRED EMBODIMENTS OF THE INVENTION

The present invention is an apparatus and method for precise and accurate determination of the volume of a liquid aliquot of a test-stock mixture formed by mixing together a test liquid of interest with a stock solution including a first dye or a first dye and a second dye. The present invention includes a system and arrangement for volume determination of a sample solution including the test-stock mixture dispensed and a diluent including the second dye. The test liquid used in the volume determination is as primarily described herein a complex and/or non-aqueous liquid as previously defined. However, the test liquid may be any liquid of choice, including an aqueous liquid, that is of interest in the calibration of a device. The present invention includes an optional kit to aid in performing some or all steps of the method described.

The test liquid may be, but is not limited to being, a liquid or liquid solution such as water, glycerol, 2-mercaptoethanol, benzene, toluene, xylene, polyethyleneglycol, piperidine, formamide, DMSO, phenol, chloroform, methanol, ethanol, dichloromethane, isopropanol, nonidet P-40, proteinase K, bovine serum albumin, fetal bovine serum, fetal calf serum, specifically, and alcohols, detergents, nucleic acid-containing solutions, protein-containing solutions, and glycerol-containing solutions, such as, but not limited to, Taq polymerase, DNA restriction exonucleases, endonucleases and ligases, and other complex or non-aqueous or complex and non-aqueous substances, generally.

Figure 1:
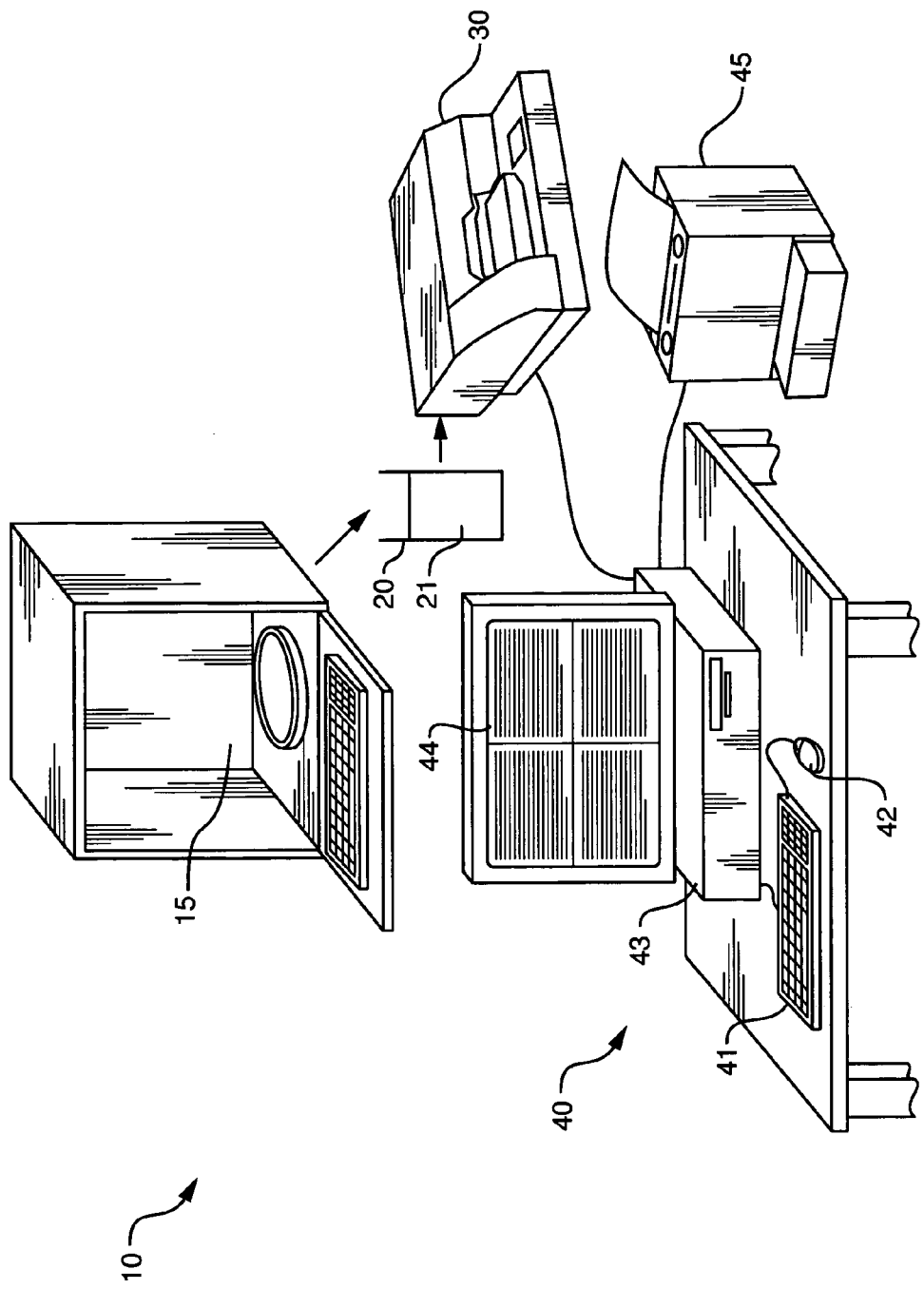
FIG. 1 is a simplified representation of an embodiment of the apparatus including an analytical balance, a liquid holder, a spectrophotometer, and a computing system.

A volume-determining apparatus 10 of the present invention, which is shown in FIG. 1, includes as primary components an analytical balance 15, a liquid holder 20, a spectrophotometer 30, and a computing system 40 capable of carrying out calculations defined through computer-executable software. The analytical balance 15 is used to weigh out multiple liquids as required by the method as discussed below. Combinations of these liquids then are mixed together to make different liquid mixtures including one or more dyes having absorbance characteristics. An aliquot 21 of each mixture is added to its own separate liquid holder 20. FIG. 1 shows only one aliquot 21 of one mixture contained in one liquid holder 20; however, it is to be understood that multiple mixture aliquots may be added to one or more liquid holders. The liquid holder 20 is placeable into the spectrophotometer 30. Liquid holders suitable for making absorbance measurements by spectrophotometer include those described in the Curtis '365 patent. The spectrophotometer 30 is capable of being instructed to initiate absorbance measurements on the liquid mixture aliquot 21, or more specifically, the liquid mixture aliquot mixed with a diluent including a dye, in the liquid holder 20. These instructions may be carried out through one or more input devices of the spectrophotometer 30 or through the computing system 40. The computing system 40 includes one or more input devices, such as a keyboard 41, a mouse 42, or a combination thereof, which may be used to input information, control the spectrophotometer 30 and/or to perform calculations of volume determination based on the absorbance measurements. Input devices may also include bar code scanners used to read bar codes associated with liquid holders and/or liquid holders containing one or more of test liquids, stock solutions, diluents, and sample solutions of the present invention. The computing system 40, including a computer processor 43 and memory storage, is configured to carry out executable-system instructions for volume determination. Input information and output information may be viewed on a computer display 44. Optionally, a local or remote printer 45 may be employed to print out input information and/or output information.

For the purpose of describing the present invention, the following terms will be used. First, a liquid of interest, including any aqueous, complex and/or non-aqueous liquid, to be used for the purpose of determining the volume of an aliquot of liquid dispensed by a liquid handling device, for example, is referred to herein as a test liquid. In general, the test liquid contains no dye subject to absorption measurements at the wavelengths of interest for the purpose of the present invention. Second, a solution including the first dye or the first dye and the second dye subject to absorption measurements, is referred to herein as a stock solution. Third, a mixture of a test liquid and a stock solution is referred to herein as a test-stock mixture. Fourth, a liquid including the second dye subject to absorption measurements and used to completely or partially fill a liquid holder, such as the well of a microtiter plate, is referred to herein as a diluent. Fifth, a mixture of test liquid and a diluent is referred to herein as a test-diluent mixture. Finally, the mixture of a test-stock mixture and a diluent, the mixture of a test liquid and a test-diluent mixture, the mixture of a stock solution and a test-diluent mixture, or the mixture of a test-stock mixture and a test-diluent mixture, any of which is the only liquid subject to absorption measurements for the purpose of the present invention, is referred to herein as a sample solution.

Some of the steps of the method of the present invention are similar to ones described in the Curtis '365 patent, but with additional and/or different steps accounting for sample solutions including the test-stock mixture. These steps are carried out using a test-stock mixture containing a first dye which absorbs at a first wavelength ($\lambda_1$) and a second dye which absorbs at a second wavelength ($\lambda_2$), a diluent containing the second dye only, and a microtiter plate with known dimensions of the wells within the plate. The steps include dispensing an aliquot of the test-stock mixture into the wells of a microtiter plate, followed by (or preceded by) dispensing diluent into the same wells within the microtiter plate. The test-stock mixture and the diluent are mixed until a homogeneous mixture is achieved, and the absorbance of the two dyes in the resultant sample solution are measured.

The volume of the aliquot of test-stock mixture dispensed into each well is determined in part based on the Beer-Lambert law shown in equation (1), which relates the measured light absorbance (A) of a sample solution to the molar absorptivity ($\epsilon$) of the dye in the sample solution, the concentration (C) of the dye in the sample solution, and the pathlength of light (l) through the sample solution:

$$A = \epsilon C l \quad (1)$$

If the concentration of dye in a sample solution is known, then the concentration can be included with the molar absorptivity to form a new constant, called the absorbance per unit pathlength (a), and equation (1) can be re-expressed as equation (2):

$$A = a \cdot l \quad (2)$$

The photometric measurements collected for each well containing a sample solution in the microtiter plate are used to calculate the aliquot volume in three steps: 1) calculation of the sample solution depth or pathlength (based on the Beer-Lambert law), 2) calculation of the total volume of sample solution, and 3) calculation of the aliquot volume.

Provided the concentration of the second dye is the same in the sample solution and in the diluent, equation (2) is used to determine the liquid depth (l) in each well, which is equivalent to the pathlength of light passed through the sample solution. By measuring the absorbance of the second dye at the second wavelength ($A_{\lambda_2}$) and incorporating the known absorbance per unit pathlength of the second dye at the second wavelength ($a_{\lambda_2}$), the sample solution depth is determined by equation (3):

$$l = \frac{A_{\lambda_2}}{a_{\lambda_2}} \quad (3)$$

Once the sample solution depth is known, the geometrical equation for the volume of the wells in the microtiter plate can be used to determine the total volume of sample solution in the wells. One common well-shape for 96-well microtiter plates is that of a truncated cone, however truncated square pyramidal shapes, and others also are commonly used. By way of example, for a truncated cone shape the calculation of the total volume ($V_T$) is based on the sample solution depth (l) as determined from equation (3), and the taper angle ($\theta$) and diameter (D) of the microtiter plate wells, as shown in equation (4):

$$V_T = \pi l \frac{D^2}{4} + \pi D l^2 \frac{\tan\theta}{2} + \pi l^3 \frac{\tan^2\theta}{3} \quad (4)$$

The calculation of the aliquot or sample volume ($V_S$) is based on the total sample solution volume ($V_T$), the measured absorbance of the second dye at the second wavelength ($A_{\lambda_2}$), the measured absorbance of the first dye at the first wavelength ($A_{\lambda_1}$), the quantities of the absorbance per unit pathlength of the second dye at the second wavelength ($a_{\lambda_2}$) and the absorbance per unit pathlength of the first dye at the first wavelength ($a_{\lambda_1}$), as given by equation (5):

$$V_s = V_T \left(\frac{a_{\lambda_2}}{a_{\lambda_1}}\right)\left(\frac{A_{\lambda_1}}{A_{\lambda_2}}\right) \quad (5)$$

This relationship is established through use of the fixed concentration of second dye in both the diluent and the test-stock mixture. By controlling this concentration, the required calculation for the total volume of sample solution becomes independent from calculation of the volume of the aliquot of the test-stock mixture within the sample solution. This allows use of equation (5) to determine the volume of aliquot of test-stock mixture in the sample solution, which corresponds to the test-stock mixture aliquot dispensed by the liquid handler, from the total volume of sample solution in the well.

Equations (3), (4) and (5) can be unified into one governing equation as shown in equation (6):

$$V_s = \frac{\pi \cdot D^2}{4 \cdot a_{\lambda_1}} \cdot (A_{\lambda_1}) + \frac{\pi \cdot D \cdot \tan\theta}{2 \cdot a_{\lambda_1} \cdot a_{\lambda_2}} \cdot (A_{\lambda_1} \cdot A_{\lambda_2}) + \frac{\pi \cdot \tan\theta}{3 \cdot a_{\lambda_1} \cdot a_{\lambda_2}^2} \cdot (A_{\lambda_1} \cdot A_{\lambda_2}^2) \quad (6)$$

Equation (6) applies to truncated cone-shaped wells in a microtiter plate. An analogous equation can be developed for wells shaped like a truncated square-based pyramid. For wells of this shape, the total volume of sample solution can be determined using the volume equation for a truncated square pyramid, as given in equation (7). Required inputs for this equation include: the pathlength of light through the solution (l, determined by equation (3)), the width of the bottom of the square well ($W_B$), the width of the top of the square well ($W_T$), and the height of the entire well (h, which is also the distance between $W_B$ and $W_T$).

$$V_{TOTAL} = (l \cdot W_B^2) + \left(\frac{l^2 \cdot W_B \cdot (W_T - W_B)}{h}\right) + \left(\frac{l^3 \cdot (W_T - W_B)^2}{3h^2}\right) \quad (7)$$

Equations (3), (7) and (5) can be combined into one governing equation for determining the sample volume dispensed into a truncated square pyramid-shaped well, as shown in equation (8):

$$V_S = \frac{W_B}{a_{\lambda_1}} \cdot (A_{\lambda_1}) + \frac{W_B \cdot (W_T - W_B)}{h \cdot a_{\lambda_1} \cdot a_{\lambda_2}} \cdot (A_{\lambda_1} \cdot A_{\lambda_2}) + \frac{(W_T - W_B)^2}{3 \cdot h^2 \cdot a_{\lambda_1} \cdot a_{\lambda_2}^2} \cdot (A_{\lambda_1} \cdot A_{\lambda_2}^2) \quad (8)$$

It is to be noted that the approaches described above may also be used in those cases where very low volumes are to be determined. In such cases, it is not necessary to include the second dye in the stock solution used in the formation of the test-stock mixture. Derived equations (6) and (8) remain applicable, with only the diluent containing the second dye because such a small volume of the test-stock mixture is added to a relatively large volume of diluent. In that case, the absence of the second dye in the sample solution will have a negligible effect on the total volume calculation, which in turn will result in a negligible effect on the calculated test-mixture aliquot volume. The present invention contemplates this optional approach for low volume determinations.

Figure 2:
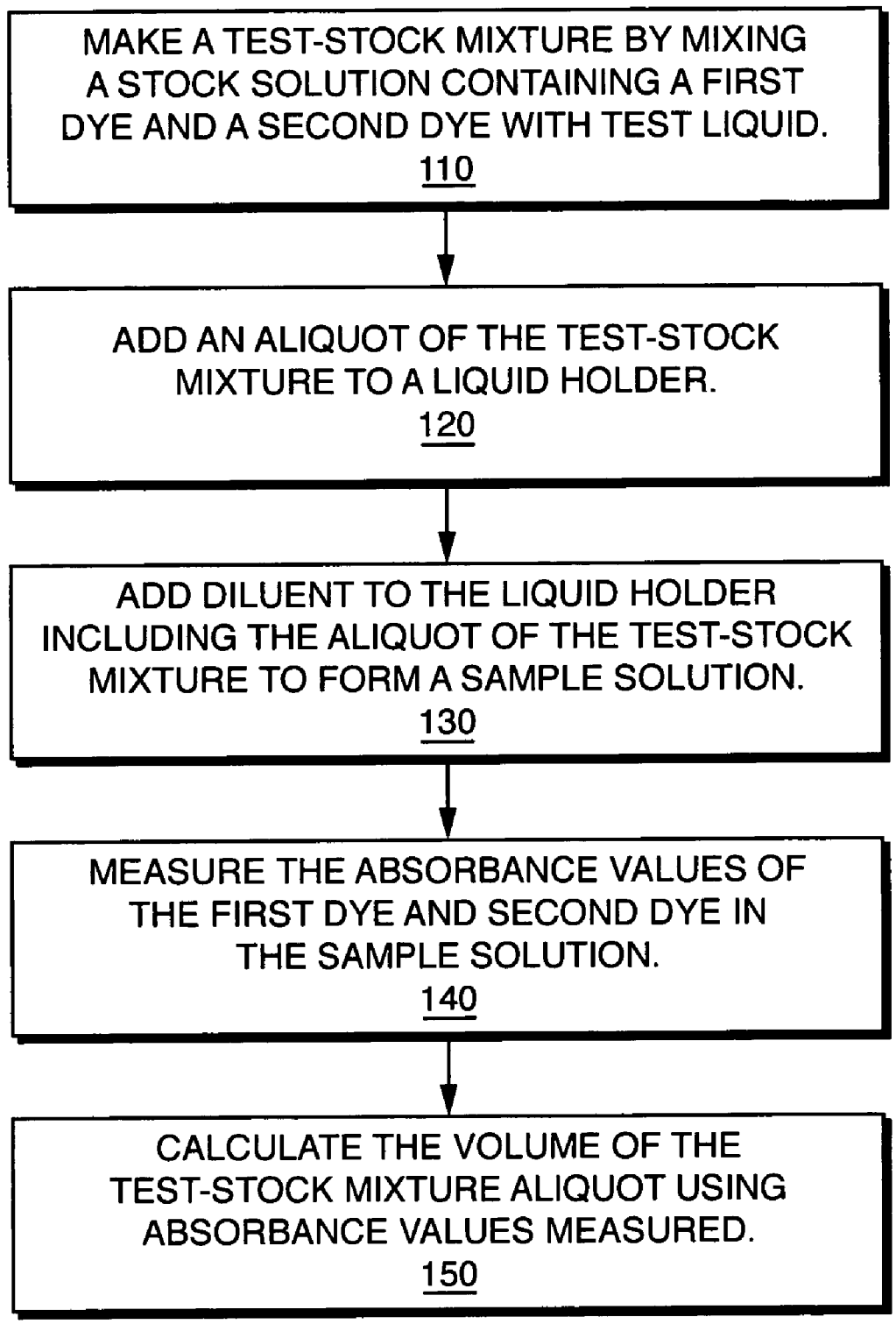
FIG. 2 is a flow diagram showing the principal steps to be taken for carrying out the method of the present invention for making the test-stock mixture and measuring absorbance values of a sample solution including the test-stock mixture.

One method 100 of the present invention for testing ALH performance with test liquids is described with reference to FIG. 2. In this method, the first dye and the second dye are included in the stock solution to aid in determining liquid volume. The first dye has an absorbance value at a first wavelength which is measurably distinguishable from an absorbance value of the second dye at the first wavelength, and the second dye has an absorbance value at a second wavelength which is measurably distinguishable from an absorbance value of the first dye at the second wavelength. The absorbance values of the dyes as contained in the stock solution are preferably provided by a supplier capable of ensuring a high degree of accuracy of the values provided. A test-stock mixture is made by mixing a known weight of a stock solution, which contains both the first dye and the second dye, with a known weight of a test liquid, step 110. By determining the mass (weight) of the test liquid and of the stock solution added, and incorporating the density of each, the volume of a particular liquid weighed and added to the mixture forming the test-stock mixture can be determined using equation (9):

$$\text{Volume} = \frac{\text{mass}}{\text{density}} \quad (9)$$

Knowing the volume of the test liquid and the stock solution, accurately weighing both and/or one or the other and then the test-stock mixture after the addition of the other, on a gravimetric balance and using equation (9) allows for an accurate determination of the dilution ratio of the test liquid by the stock solution to be calculated from equation (10):

Dilution Ratio=(Volume Stock Solution)/(Volume Stock Solution+Volume Test Liquid) (10)

Accurately knowing this dilution ratio allows for an accurate calculation of the absorbance per pathlength of either dye in the test-stock mixture, which allows for accurate determination of the volume of test-stock mixture dispensed by a liquid handler under calibration. That is, the dilution ratio is used to calculate a revised absorbance per pathlength of the first dye and the second dye through the following equation:

$a'_\lambda = a_\lambda \cdot$ Dilution Ratio (11)

where the new absorbance per pathlength ($a'_\lambda$) is determined as the product of the absorbance per pathlength from the stock solution, and the Dilution Ratio of that stock solution. This new or revised absorbance per pathlength is substituted into the calculations of volume for which dye absorbance per pathlength values are required.

The method described above enables determination of suitable dilution ratios for the purpose of being capable of measuring absorbance values in specified volume ranges. Additional accuracy of determination may be achieved by accounting for fluctuations, if any, in relative test liquid and stock solution densities as a function of atmospheric conditions. This optional approach is carried out by determining a z-correction factor (z), which accounts for the buoyancy factor of air, and density changes as a function of atmospheric temperature, pressure and humidity. Using these factors, a more accurate volume can be calculated using equation (12):

Volume=mass·(z/Relative Density) (12)

The volume information obtained from equation (12) may then be plugged into equation (10). The Relative Density is determined through a process such as the process described in the description herein of the formation of the stock solution 1 and stock solution 2 of the stock solutions for the Example.

Once a test-stock mixture has been prepared, an aliquot of the test-stock mixture is added to a well of a liquid holder, step 120. A diluent including the second dye is then added to the same well to make up a portion of the volume in the well, step 130. Alternatively, the diluent may be added to the well before the test-stock mixture. The test-stock mixture and the diluent are mixed together to form a sample solution. The absorbance of the sample solution in the liquid holder is measured at the first wavelength and at the second wavelength by a plate reader, step 140. Finally, the absorbance values measured in step 140 are used to calculate the volume of the aliquot of test-stock mixture, step 150 using the equations previously described herein. It is to be noted that an alternative of the method shown in FIG. 2 includes the use of a stock solution containing only the first dye and none of the second dye. That alternative arrangement is suitable when the volumes to be determined are relatively small. In that case, the absence of the second dye in the sample solution is negligible in the calculation.

The particular ratios of test liquid to stock solution are preferably chosen such that the new absorbance per pathlength carries over to measurable absorbance values of the sample solution being tested. That is, the concentration of either or both of the first and second dyes in the sample solution is in a measurable absorbance range. They are chosen to cover a desired test volume range, therefore, they may or may not be different for any particular sample solution from one volume range to another. For the purpose of this description, the test volume range is based upon the final absorbance values that will be measured by the plate reader. Examples of test-stock mixtures and particular ratios are presented herein. It is to be noted that the ratios are functions of the particular liquids of choice in the volume determination. In general, the present invention is directed to the use of any selectable liquid as the test liquid, and a stock solution of known characteristics, such as an aqueous stock solution, and combining them together to form the test-stock mixture having measurable absorbance values. The resultant test-stock mixture preferably includes flow characteristics corresponding to the flow characteristics of the test liquid while maintaining the ability to distinguish the absorbance values associated with the first dye and the second dye when the test-stock mixture and diluent are combined to form a sample solution that is measured for absorbance characteristics.

An optional aspect of the present invention is the creation of a test-stock starter mixture. While the description of the present invention has been directed primarily to the instructions for forming the test-stock solution, it is contemplated that a manufacturer, rather than an end user, may produce and provide a prepared test-stock starter mixture including a test liquid of interest to an end user, and a stock solution including the first dye or the first dye and the second dye. The prepared test-stock starter mixture may then be combined with a diluent as described above and the resultant sample solution subject to absorbance measurements. In that way, the end user may omit the steps of preparing the test-stock mixture, including making the required weight measurements, relying instead on the commercial manufacturer to perform those steps instead.

The first dye referred to herein may be any compound which selectively absorbs light, and the second dye referred to herein may be any other compound which selectively absorbs light, with the only limitation being that the first dye must have an absorbance value at a first wavelength which is measurably distinguishable from an absorbance value of the second dye at the first wavelength, and the second dye must have an absorbance value at a second wavelength which is measurably distinguishable from an absorbance value of the first dye at the second wavelength. Exemplary compounds which may be used as the first dye and the second dye are listed in the Curtis '365 patent. In addition, stock solution options suitable in the formation of the test-stock mixture of the present invention are also described in the Curtis '365 patent.

The method of the present invention is more specifically described with reference to an Example; however, it is not to be construed as being limited thereto. In particular, while the following Example describes instruction for determining the volumes of aliquots of test-stock mixtures including dimethyl sulfoxide (DMSO) specifically as the test liquid, the method is not to be construed as being limited to being used to determine the volumes of aliquots of test-stock mixtures including DMSO only. The method may be used to determine the volume of an aliquot of any test-stock mixture including any test liquid of choice. The stock solutions, diluents, and devices, mixing, measurement and determination methods described in the article entitled "Multichannel Verification System (MVS™): A Dual-Dye Ratiometric Photometry System for Performance Verification of Multichannel Liquid Delivery Devices" written by several of the present inventors for the assignee of the present invention and published in the journal JALA in February 2005 were used to perform part of the steps used in evaluating the test-stock mixtures of the Example. The contents of that publication are incorporated herein by reference. The Example information is presented in Table 2 (for a 96-well plate) and in Table 3 (for a 384-well plate) herein.

EXAMPLE

Solutions Used

In this Example, the volumes of a plurality of aliquots of mixtures of DMSO test liquid in aqueous stock solution were determined by using the method of the present invention. As a first step of this method, two different formulations of stock solution and three different formulations of test-stock mixture were prepared. For the purposes of this Example, these five liquids are specifically referred to as being "stock solution 1", "stock solution 2", "test-stock mixture B", "test-stock mixture C", and "test-stock mixture D." Stock solutions 1 and 2 were prepared as described in the following two paragraphs. It is to be noted that stock solutions described in the Curtis '365 patent may also be used in the alternative.

Stock solution 1 was manufactured to have an absorbance of 739.2 at 520 nm in a 1 cm pathlength cuvette, and no significant absorbance at 730 nm. This solution was prepared by dissolving only the first dye, a red dye component, (that absorbs at 520 nm) into a previously prepared preserved diluent containing no dye component. The preserved diluent was prepared by dissolving 0.30 grams Proclin (a preservative) into one liter of deionized water. The freshly mixed preserved diluent was filtered through a 0.2 micron filter and stored in a tightly capped glass bottle. Stock solution 1 was prepared by dissolving 1,005 grams of Ponceau S into the preserved diluent to a total batch size of one liter. The relative density of the stock solution 1, as compared to deionized water, was measured with a pynknometer. The representative absorbance per a 1 cm pathlength of stock solution 1 at 520 nm was determined by making an accurate dilution of 0.05 mL stock solution 1 to 30 mL preserved diluent. The dilution of stock solution 1 and preserved diluent was thoroughly mixed, capped and allowed to thermally equilibrate. The absorbance in a 1 cm pathlength cuvette was measured for the dilution (0.05/30) at 520 nm. The absorbance per pathlength was determined by applying the absorbance measured for the dilution by the dilution factor indicated above. The batch stock solution 1 was adjusted to an absorbance of 739.2±0.25% at 520 nm in a 1 cm pathlength cuvette.

Stock solution 2 was manufactured to have a target absorbance of 75 in a 1 cm pathlength cell at a wavelength of 520 nm, and an absorbance of 0.610 in a 1 cm pathlength cell at a wavelength of 730 nm. Stock solution 2 was prepared by dissolving the red dye component (that absorbs at 520 nm) into a previously prepared diluent containing the second dye, referred to herein as the blue dye component, (absorbs at 730 nm). The diluent was prepared by dissolving 0.30 grams Proclin, 4.0709 grams potassium hydrogen phthalate (KHP, a buffer salt), 1.1384 grams copper chloride (dihydrate), and 3.8720 grams EDTA (ethylenediaminetetraacetic acid, tetrasodium salt, a chelator for the ionic copper) into deionized water, to a total batch volume of one liter. The relative density of the diluent, as compared to deionized water, was measured with a pynknometer. The pH of the diluent was adjusted to a value of 6.0±0.05 pH units by the addition of either hydrochloric acid (if the pH is higher than 6.05), or sodium hydroxide (if the pH is lower than 5.95). The absorbance at 730 nm was measured in a 1 cm pathlength cell and adjusted to 0.610±0.1%. The diluent was filtered through a 0.2 micron filter and stored in a tightly capped glass bottle. Stock solution 2 was prepared by dissolving 1.47 grams of Ponceau S into the diluent to a total batch size of 1 liter. The relative density of this stock solution 2, as compared to deionized water, was measured with a pynknometer. The representative absorbance per a 1 cm pathlength of the solution at 520 nm was determined by making a dilution to bring the stock solution 2 to a measurable absorbance range (e.g., 1 mL stock solution into 29 mL blank solution). The dilution was thoroughly mixed, capped and allowed to thermally equilibrate. The absorbance in a 1 cm pathlength cuvette was measured at 520 nm, and the representative absorbance for the stock solution 2 was determined by multiplying the dilution absorbance by the ratio of the stock solution to the precursor. The stock solution 2 was adjusted to an absorbance of 75±1% at 520 nm in a 1 cm pathlength cuvette, and to an absorbance of 0.6103±0.1% at 730 nm in a 1 cm pathlength cuvette.

Figure 3A:
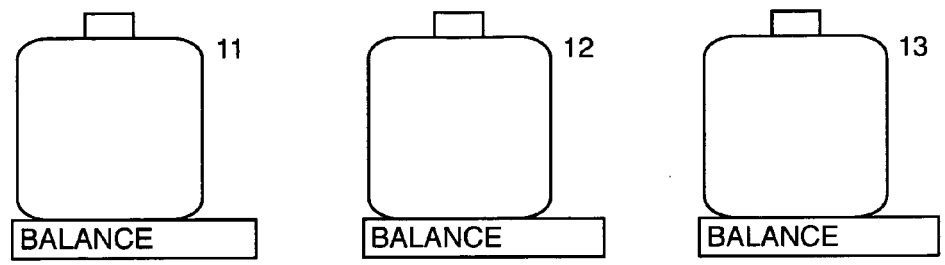
FIGS. 3A-3C show a flow diagrams illustrating the steps of making three different test-stock mixtures of the Example used in describing the present invention.
Figure 3B:
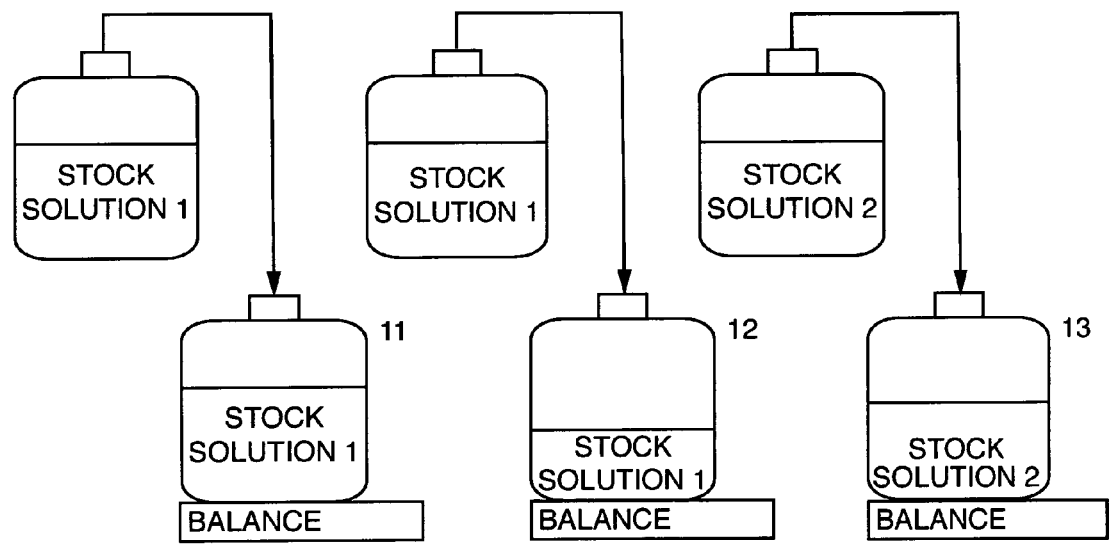
Figure 3C:
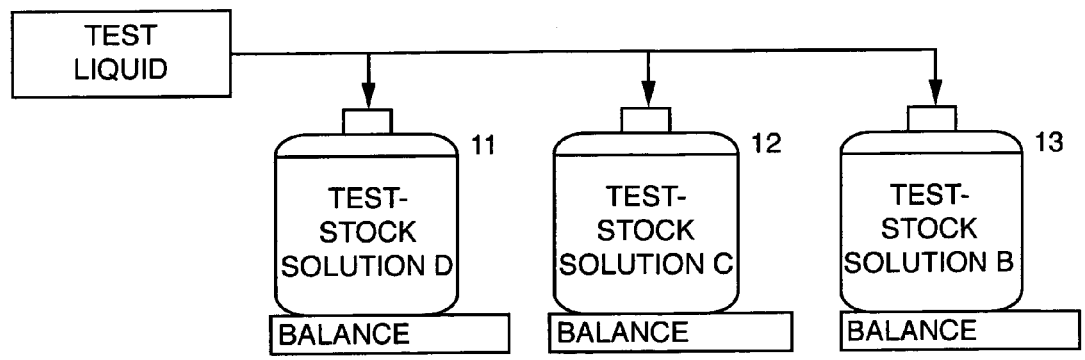

With reference to FIGS. 3A-3C, test-stock mixture D was prepared by mixing 7.0 g of stock solution 1 with 22.96 g of essentially pure DMSO as the test liquid to make a 25% (vol/vol) solution of stock solution 1 in DMSO. As shown in FIG. 3A, an empty bottle 11 was weighed on a balance 15. As shown in FIG. 3B, the stock solution 1 then was added to the weighed bottle 11 until the balance indicated that 7.0 g of stock solution 1 had been added. The gram weight of stock solution 1 was chosen based primarily on the consideration that the gram weight of stock solution 1 be large enough to make enough test-stock mixture D to carry out this particular application of the method, and the gram weight of the DMSO required was calculated by using the formula, $\gamma=3.28(x)$, wherein x is the gram weight of stock solution 1, and $\gamma$ represents the gram weight of DMSO required to make a 25% (vol/vol) solution of stock solution 1 in DMSO. The number given in this example (i.e., "3.28" from the equation $\gamma=3.28x$) corresponds to a multiplier needed to make a final test-stock mixture with an absorbance per pathlength that can be used to test volumes over a certain range. Using this number allows the user to determine how much stock solution and how much test liquid are needed to make a desired amount of test-stock mixture that the user wants to make. This multiplier is approximately the inverse of the Dilution Ratio previously described herein. The same concept applies for all test-stock mixture examples described herein. As shown in FIG. 3C, the desired amount of the test liquid, which specifically was 22.96 g of essentially pure DMSO, was added to the stock solution 1 in bottle 11 while it was being weighed on the balance 15 to complete the preparation of test-stock mixture D.

Test-stock mixture C was prepared by mixing 3.0 g of stock solution 1 in 29.837 g of essentially pure DMSO as the test liquid to make a 9.9% (vol/vol) solution of stock solution 1 in DMSO. As shown in FIG. 3A, an empty bottle 12 was weighed on a balance 15. As shown in FIG. 3B, the stock solution 1 then was added to the weighed bottle 12 until the balance indicated that 3.0 g of stock solution 1 had been added. The gram weight of stock solution 1 was chosen based primarily on the consideration that the gram weight of the stock solution 1 be large enough to make enough test-stock mixture C to carry out this particular application of the method, and the gram weight of the DMSO required was calculated by using the formula, $\gamma=9.9457(x)$, wherein x is the gram weight of stock solution 1, and $\gamma$ represents the gram weight of DMSO required to make a 9.9% (vol/vol) solution of stock solution 1 in DMSO. As shown in FIG. 3C, the desired amount of the test liquid, which specifically was 29.837 g of essentially pure DMSO, was added to the stock solution 1 in bottle 12 while it was being weighed on the balance 15 to complete the preparation of test-stock mixture C.

Test-stock mixture B was prepared by mixing 6.0 g of stock solution 2 in 25.92 g of essentially pure DMSO as the test liquid to make a 20.2% (vol/vol) solution of stock solution 2 in DMSO. As shown in FIG. 3A, an empty bottle 13 was weighed on a balance 15. As shown in FIG. 3B, the stock solution 2 then was added to the weighed bottle 13 until the balance indicated that 6.0 g of stock solution 2 had been added. The gram weight of stock solution 2 was chosen based primarily on the consideration that the gram weight of the stock solution 2 be large enough to make enough test-stock mixture B to carry out this particular application of the method, and the gram weight of the DMSO required was calculated by using the formula, $\gamma=4.32(x)$, wherein x is the gram weight of stock solution 2, and $\gamma$ represents the gram weight of DMSO required to make a 20.2% (vol/vol) solution of stock solution 2 in DMSO. As shown in FIG. 3C, the desired amount of the test liquid, which specifically was 25.92 g of essentially pure DMSO, was added to the stock solution 2 in bottle 13 while it was being weighed on the balance 15 to complete the preparation of test-stock mixture C.

The ratio values identified above for the three different mixtures were selected to achieve test-stock mixtures for DMSO as the test liquid in order to conform with the volume ranges of commercially-available aqueous-based stock solutions, such as the stock solutions designated as MVS Sample Solutions Range D, C and B available from Artel of Westbrook, Maine. These or other values may be used for other solvents as test liquids, dependent upon the particular density of the solvent and its affect, if any, on the absorbance characteristics of the dye(s). It may be necessary to conduct trial-and-error evaluations of mix ratios for compatibility of the test liquid with the selected stock solution, the volume range(s) of interest, and the ability to distinguish between the first and second dye. All solutions of the Example were allowed to equilibrate to within a temperature range of about 18° C. to about 25° C. prior to being used.

Choice of Liquid Holder and Volume and Type of Alternative Solution Determined

A portion of the Example aliquots ranged in volume from 0.4 µl to 49.9 µl. The absorbances of these aliquots, were measured in a liquid holder that was a 96-well microtiter plate. The remainder of the Example aliquots ranged in volume from 0.1 µl to 9.9 µl. The absorbances of these remaining aliquots were measured in a liquid holder that was a 384-well microtiter plate. The particular test-stock mixture, either test-stock mixture B, test-stock mixture C, or test-stock mixture D, used for any particular aliquot was chosen based on the expected volume of the aliquot according to the parameters shown in the following Table 1:

TABLE 1

| Volume of Test-Stock Mixture Added | Compatible Test-Stock Mixture |
|---|---|
| 96-wells { 0.4 µL-4.3 µL | Test-Stock Mixture D |
| 1.8 µL-10.9 µL | Test-Stock Mixture C |
| 9.1 µL-49.9 µL | Test-Stock Mixture B |
| 384-wells { 0.1 µL-1.1 µL | Test-Stock Mixture D |
| 0.5 µL-2.8 µL | Test-Stock Mixture C |
| 2.3 µL-9.9 µL | Test-Stock Mixture B |

Referring to Table 1 above, in all cases where ranges of volumes of test-stock mixture overlap (left column), two test-stock mixtures are listed as being appropriate for use. For any particular aliquot having an expected volume which fell within any of these overlapping ranges, only one of the two appropriate test-stock mixtures, chosen arbitrarily, was used.

Determining Volume

Figure 4:
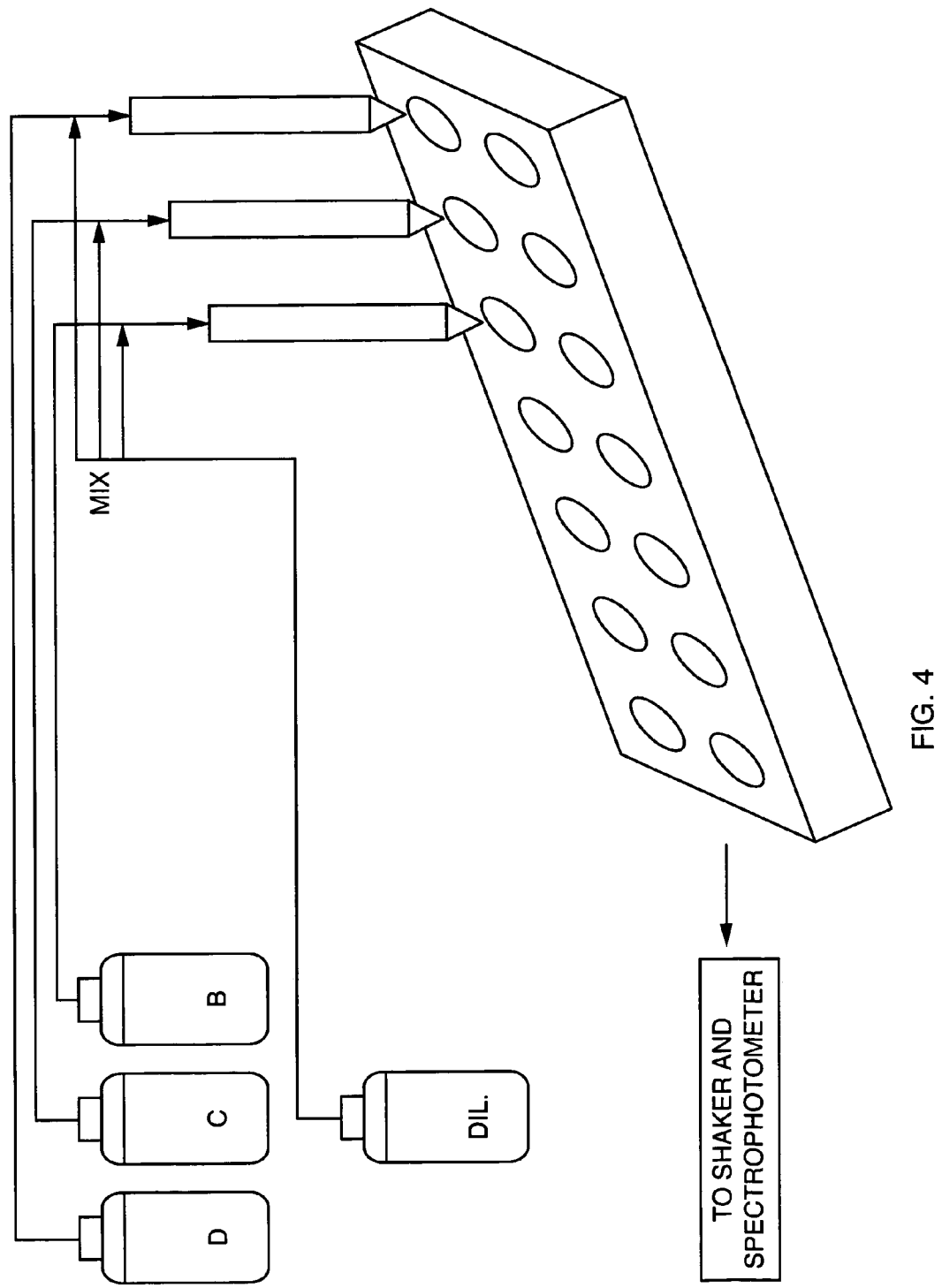
FIG. 4 is a flow diagram illustrating the steps for combining the test-stock mixtures of FIG. 3 with a diluent to make sample solutions used to determine volume dispensed from a liquid holder.

With reference to FIG. 4, determination of all volumes was performed by using the apparatus of the invention, one embodiment of which is shown in FIG. 1 and alternatives or detailed versions of which are described in the JALA publication and the Curtis '365 patent referenced herein. Generally, an aliquot of each test-stock mixture 21 was dispensed into its own liquid holder 20, which was an individual well of a microtiter plate. To this aliquot, the working volume was adjusted to 200 µL in each well of the 96-well plate, or to 55 µL in each well of the 384-well plate, by adding diluent. For example, if 2 µL of test-stock mixture C was added to a well within the 96-well plate, 198 µL of diluent was added to create a working volume of 200 µL, and if 8 µL of test-stock mixture B was added to a well within the 384-well plate, 47 µL of diluent was added to create a working volume of 55 µL. Once the working volume was achieved in each well, a plate shaker device was used to properly mix the sample solutions formed by the combination of the test-stock mixture and the diluent. Each plate including a sample solution was placed into the spectrophotometer 30 connected to a computing system 40 capable of carrying out volume determination measurements through computer-executable software.

Prior to making any absorbance measurements, the software was run on the computing system 40 and displayed on the computing system display 44, and pre-absorbance measurement entries were made. For instance, the user must enter the characteristics of the test-stock mixture into the software before absorbance measurements are acquired. In order to use the computer, associated software and components of the measurement system to determine the dispensed volume of the test-stock mixture, information required for the volume determinations must be entered, such as density values of the test liquid and stock solution, stock solution absorbance per pathlength, weight of stock solution, and weight of test liquid. Entering the noted information may be achieved through direct manual entry, or through local or remote information exchange techniques including, but not limited to, bar codes on one or more components of the invention made readily through bar code scanners connectable to the computing system 40.

Figure 5:
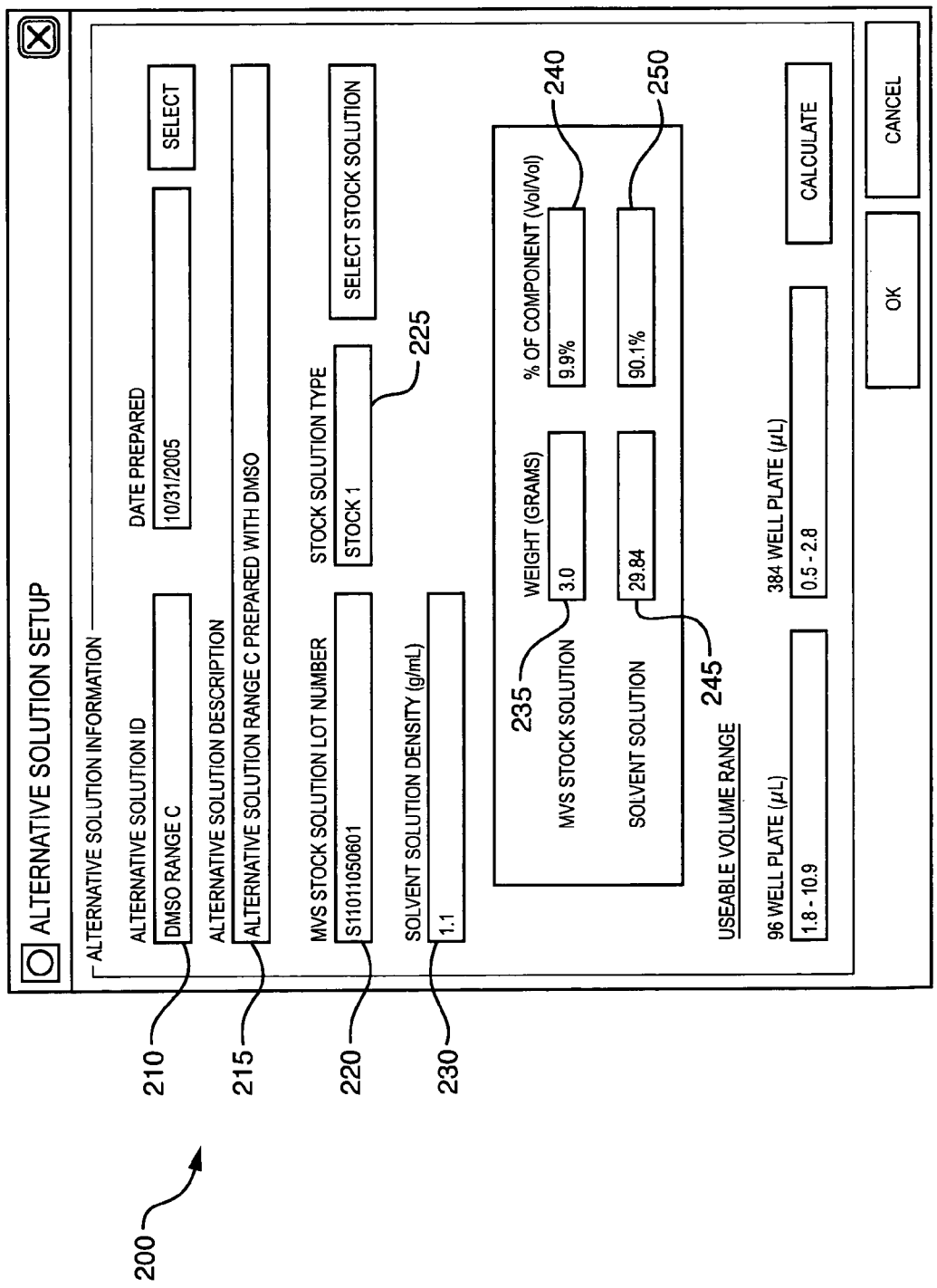
FIG. 5 is one representative image of information displayed on a computer display of the apparatus prior to carrying out the dual-dye, dual wavelength ratiometric photometry method.

FIG. 5 is a representative image as seen on the computer display 44 after all such entries were made in the computing system 40. Generally, this image is a first window 200 into which an arbitrarily-chosen test-stock mixture identifier may be entered into a box within the window 200 labeled "Alternative Solution ID" 210, an arbitrarily-chosen descriptive identifier may be entered into a box labeled "Alternative Solution Description", and the lot number and type of the stock solution used may be entered into boxes labeled "MVS Stock Solution Lot Number" 220 and "Stock Solution Type" 225, respectively. The first window 200 also has a box, which is labeled "Solvent Solution Density (g/mL)" 230, for entering the density of the test liquid. Other information that is entered into the first window 200 is the gram weight 235 of the stock solution and the gram weight 245 of the test liquid (which is referred to in the image as being a "solvent solution", which for the purposes of the present invention is any complex and/or non-aqueous liquid). Once the weights are entered, the software calculates the test liquid's percent composition 240 of the test-stock mixture and the stock solution's percent composition 250 of the test-stock mixture, on a volume-to-volume basis.

Figure 6:
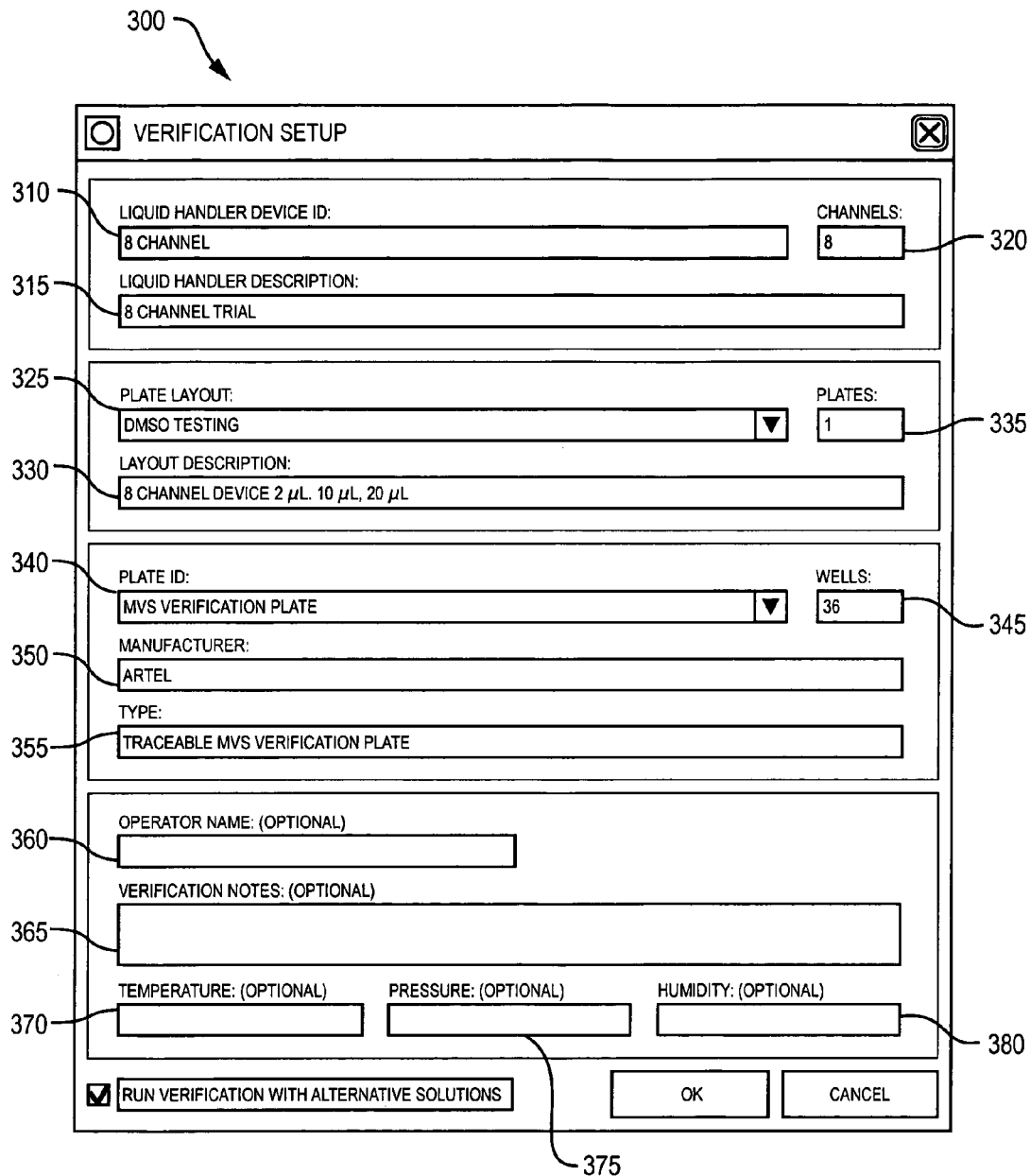
FIG. 6 is one representative image of information displayed on a computer display of the apparatus during the course of carrying out the dual-dye, dual wavelength ratiometric photometry method.

Information regarding the identification 310, description 315, and number of channels 320, of the particular dispensing device used was entered into a second window 300, a representative example of which is reproduced in FIG. 6. Other information that was entered into this second window 300 included information pertaining to plate layout 325, plate layout description 330, number of plates being used 335, plate identification 340, number of wells within the plate 345, plate manufacturer identification 350, and type of plate 355. Additionally, the second window 300 provides boxes into which may be entered, at the operator's option, information regarding operator name 360, notes 365, temperature 370, pressure 375, and humidity 380. Entry of the noted information may be achieved through direct manual entry, or through local or remote information exchange techniques including, but not limited to, bar codes on one or more components of the invention made readily through bar code scanners connectable to the computing system 40.

After the aforementioned information was entered as described above and shown in FIG. 4, and the test-stock mixtures in the indicated ratios made, the mixtures were combined with the diluent in one or more wells of the microtiter plate in the ratios indicated herein, and the combination mixed within the wells using a plate shaker (or other means of mixing), to produce sample solutions for absorbance testing. The computing system 40 was used to direct the software to make absorbance readings of the sample solutions. That is, sample solutions including aliquots of test-stock mixtures B, C and D were measured. These measurements were specifically performed by placing the multi-well plate in a spectrophotometer 30, directing the spectrophotometer 30, via the computing system 40, to measure each well at the first wavelength, which specifically was 520 nm, and then again at the second wavelength, which specifically was 730 nm. Once such absorbance values were measured, the software of the computing system 40 calculated total sample solution volume and then determined the volume for each test-stock mixture aliquot added to a well. Volume determination data generated for the plurality of test-stock mixture aliquots included in this Example are shown below in Tables 2 and 3.

TABLE 2

Three different test-stock mixtures dispensed into 9 columns of 96-well microtiter plate; three repeat dispenses performed per test-stock mixture; aliquots dispensed with 8-channel handheld pipette; DMSO-based test-stock Mixtures for D, C, and B; aqueous diluent (with $2^{nd}$ dye) added after test-stock mixture added to create working volume of 200 µL in each well; Columns 1-3 test-stock mixture D with target aliquot of 2 µL; Columns 4-6, mixture C with target aliquot of 8 µL; and Columns 7-9, mixture B with target aliquot of 20 µL.

|   | Test-Stock Mixture D, 2 uL | | | Test-Stock Mixture C, 8 uL | | | Test-Stock Mixture B, 20 uL | | |
|---|---|---|---|---|---|---|---|---|---|
|   | 1 | 2 | 3 | 4 | 5 | 6 | 7 | 8 | 9 |
| A | 1.948 | 1.981 | 1.977 | 8.089 | 8.098 | 8.128 | 20.23 | 20.43 | 20.18 |
| B | 1.957 | 2.035 | 2.005 | 8.191 | 8.151 | 8.127 | 20.28 | 20.39 | 20.39 |
| C | 2.002 | 2.021 | 2.009 | 8.135 | 8.152 | 8.138 | 20.37 | 20.41 | 20.31 |
| D | 1.973 | 1.987 | 1.922 | 8.096 | 8.055 | 8.07  | 20.23 | 20.3  | 20.3  |
| E | 2.019 | 2.038 | 2.012 | 8.141 | 8.128 | 8.099 | 20.51 | 20.41 | 20.36 |
| F | 1.984 | 2.006 | 1.993 | 8.058 | 8.123 | 8.128 | 20.32 | 20.41 | 20.25 |
| G | 2.01  | 2.023 | 2.006 | 8.104 | 8.084 | 8.123 | 20.32 | 20.41 | 20.41 |
| H | 2.115 | 2.103 | 2.054 | 8.071 | 8.133 | 8.123 | 20.2  | 20.32 | 20.09 |

The table below shows the calculated output data for mean, relative inaccuracy %, standard deviation and CV % for the different test-stock mixtures dispensed in replicates of three into a 96-well microtiter plate.

TABLE 3

|   | Test-Stock Mixture, Target Volume | | |
|---|---|---|---|
|   | Mixture D, 2 uL | Mixture C, 8 uL | Mixture B, 20 uL |
| Mean Volume (uL) | 2.008 | 8.114 | 20.33 |
| Relative Inaccuracy % | 0.40% | 1.43% | 1.65% |
| Standard Deviation | 0.043 | 0.033 | 0.1 |
| CV % | 2.14% | 0.41% | 0.49% |

Calibrated syringes were employed to dispense aliquots of DMSO-based test-stock mixtures D, C, and B. These aliquot volumes, as shown in the tables below, were dispensed into individual wells of a 384-well microtiter plate. Each well was back-filled with enough volume of diluent to fill each well to 55 µL of total working volume. The target volumes are shown directly after the test-stock mixture ID, i.e., test-stock mixture D, 1 µL where 1 µL is the target volume for the volume verification.

The table shows the raw data for 8 aliquot dispenses from a calibrated syringe. All test-stock mixtures were dispensed 8 times into 8 individual wells. In column 1 of the plate, test-stock mixture D was dispensed; into column 2 of the plate, test-stock mixture C was dispensed and into column 3, test-stock mixture B was dispensed.

|   | Test-stock mixture D, 1 uL | Test-stock mixture C, 2 uL | Test-stock mixture B, 8 uL |
|---|---|---|---|
| A | 1.05  | 2.054 | 8.91 |
| B | 1.01  | 2.037 | 8.51 |
| C | 1.065 | 2.024 | 8.31 |
| D | 1.051 | 2.068 | 8.31 |
| E | 1.035 | 2.041 | 8.31 |
| F | 1.034 | 2.067 | 8.26 |
| G | 1.054 | 2.043 | 8.3  |
| H | 1.054 | 2.032 | 8.22 |

The table below shows the calculated output data for mean, relative inaccuracy %, standard deviation and CV % for the different test-stock mixtures dispensed in replicates of 8 into 8 individual wells of a 384-well microtiter plate.

|   | Test-stock mixture D, 1 uL | Test-stock mixture C, 2 uL | Test-stock mixture B, 8 uL |
|---|---|---|---|
| Menu (uL) | 1.044125 | 2.04575 | 8.39125 |
| Relative Inaccuracy % | 3.38% | 2.29% | 5.02% |
| Standard Deviation | 0.017166724 | 0.015962008 | 0.22611233 |
| CV % | 1.64% | 0.78% | 2.69% |

In another embodiment of the present invention, a test-diluent mixture is created. Using the techniques described herein regarding the combination of a test liquid with a stock solution, the diluent may be used as a substitute for the stock solution. The resultant test-diluent solution including the second dye contained in the diluent, may be used in the formation of a sample solution to be tested for absorbance measurements of the first and second dyes. A test-diluent mixture is made by mixing a known weight of a diluent, which contains only the second dye, with a known weight of a test liquid. By determining the mass (weight) of the test liquid and of the diluent added together, and incorporating the density of each, the volume of a particular liquid weighed and added to the mixture forming the test-diluent mixture can be determined using equation (9). Knowing the volume of the test liquid and the diluent, accurately weighing both and/or one or the other and then the test-diluent mixture after the addition of the other, on a gravimetric balance and using equation (9), allows for an accurate determination of the dilution ratio of the diluent by the test liquid using equation (10). Accurately knowing this dilution ratio allows for an accurate calculation of the absorbance per pathlength of the second dye in the test-diluent mixture, which allows for accurate determination of the volume of the liquid dispensed by a liquid handler under calibration through the equations presented herein for a sample solution including the test-diluent mixture. That is, the dilution ratio is used to calculate a revised absorbance per pathlength of the second dye through equation (11). This new or revised absorbance per pathlength is substituted into the calculations of volume for which dye absorbance per pathlength values are required.

The method described above enables determination of suitable dilution ratios for the purpose of being capable of measuring absorbance values in specified volume ranges. Additional accuracy of determination may be achieved by accounting for fluctuations, if any, in relative test liquid and diluent densities as a function of atmospheric conditions. This optional approach is carried out by determining a z-correction factor (z), which accounts for the buoyancy factor of air, and density changes as a function of atmospheric temperature, pressure and humidity. Using these factors, a more accurate volume can be calculated using equation (12). The test-diluent mixture may include any diluent of interest including, but not limited to, the diluents described herein and in the Curtis '365 patent. The test-diluent mixture may be combined with a stock solution including either the first dye alone or the first dye and the second dye, or with a test-stock mixture including either the first dye alone or the first dye and the second dye.

An optional aspect of the test-diluent mixture of present invention is the creation of a test-diluent starter mixture. While the description of the present invention has been directed primarily to the instructions for forming the test-stock solution, it is contemplated that a manufacturer, rather than an end user, may produce and provide a prepared test-diluent starter mixture including a test liquid of interest to an end user, and a diluent including the second dye only. The prepared test-diluent starter mixture may then be combined with a stock solution, a test-stock mixture, or a test-stock starter mixture and the resultant sample solution subject to absorbance measurements. In that way, the end user may omit the steps of preparing the test-diluent mixture, including making the required weight measurements, relying instead on the commercial manufacturer to perform those steps instead.

Another optional aspect of the present invention is the way in which either or both of the stock solution and the diluent are made available to a user making a sample solution to be subjected to absorbance measurements. While the discussion of the present invention herein has been directed to the existence of a stock solution or a diluent in liquid form, it is contemplated that the user may be provided with either or both of the first dye and the second dye in a form other than solubilized in a liquid. For example, it may be provided to the user as a solid, such as a powder. The user may also be provided with a liquid to be combined with the separate dye material, and the two mixed together to form either the stock solution or the diluent. In this optional arrangement, the user is provided with instructions to produce the stock solution or the diluent of interest. The instructions include steps for making the stock solution or the diluent by adding a known weight of the dye, preferably but not limited to powder form, with a specified volume of a liquid of choice, such as an aqueous liquid, a complex liquid, and/or a non-aqueous liquid. The two are combined to produce a stock solution or a diluent having known absorbance characteristics of the first dye and the second dye. For example, the methods for making the stock solution 1 and stock solution 2 of the Example described herein represent example steps to be used in the production of a stock solution, or relatedly, a diluent, using either or both of the first dye and the second dye.

A kit of the present invention contains instructions for carrying out one or more embodiments of the methods described herein, and also contains one or more items which may be used to carry out the methods. Such items may be, but are not limited to being, one or more stock solutions, one or more dyes which may be used as the first dye or the second dye, one or more diluents, one or more liquid holders, or computer-executable software. The items may also include the dyes in solubilized or separate form, with instructions for a user to produce a stock solution, a diluent, or both, using a solubilizing liquid of choice. More specific embodiments of the kit are described in the Curtis '365 Patent.

The computer-executable software includes computer-readable signals tangibly embodied on the computer-readable medium, where such signals define instructions for processing data obtained from the spectrophotometer. Such instructions may be written in any of a plurality of programming languages, for example, Java, XML Visual Basic, C, or C++, Fortran, Pascal, Eiffel, Basic, COBOL, and the like, or any of a variety of combinations thereof. The computer-readable medium on which such instructions preferably reside is readable by the central processing unit of the computing system. Further, the steps of processing the data obtained from the spectrophotometer may be performed in alternative orders, in parallel and serially.

It is to be understood that various modifications may be made to the apparatus, the method, and/or the kit without departing from the spirit and scope of the invention. For example, the steps of the method may be performed in differing order, one or more steps may be omitted, and one or more steps may be replaced with alternative forms thereof. Accordingly, other embodiments are within the scope of the claims appended hereto.

What is claimed is:

1. A method to create a test-stock mixture to be used in the determination of a volume of the test-stock mixture to be dispensed from a liquid handling device to be calibrated, the test-stock mixture including a test liquid of interest, the method comprising the step of mixing the test liquid with a stock solution, which stock solution includes a first dye with a known absorbance characteristic to form the test-stock mixture, wherein a ratio of test liquid to stock solution is selected to establish for the test-stock mixture flow characteristics that correspond to flow characteristics of the test liquid before mixing with the stock solution while maintaining in the test-stock mixture a distinction between the known absorbance characteristic of the first dye in the stock solution and a known absorbance characteristic of a second dye.

2. The method of claim 1 wherein the step of mixing includes the step of mixing the test liquid and the stock solution in a weight ratio as a function of the density of the stock solution and the density of the test liquid.

3. The method of claim 1 further comprising the step of calculating a dilution ratio of the stock solution by the test liquid in the test-stock mixture.

4. The method of claim 3 further comprising the step of determining a z-correction factor for fluctuations in density values of the test liquid and the stock solution.

5. The method of claim 1 wherein the stock solution includes the second dye.

6. The method of claim 1 wherein the known absorbance characteristic of the first dye of the stock solution includes an absorbance per pathlength of the first dye, the method further comprising the step of determining a revised absorbance per pathlength of the first dye in the test-stock mixture.

7. The method of claim 1 wherein the known absorbance characteristic of the second dye includes an absorbance per pathlength of the second dye, the method further comprising the step of determining a revised absorbance per pathlength of the second dye in the test-stock mixture.

8. A method for determining the volume of a liquid aliquot to be dispensed from a handling device, comprising the steps of:
   a. making a test-stock mixture by mixing a test liquid having a known weight and a known density value with a stock solution having a known weight and a known density value, the stock solution including a first dye with a known absorbance characteristic;
   b. adding an aliquot of the test-stock mixture to a liquid holder;
   c. adding a diluent to the test-stock mixture in the liquid holder to produce a sample solution, the diluent including only a second dye having a known absorbance characteristic different from the known absorbance characteristic of the first dye, wherein a ratio of the known weight of the test liquid to the known weight of the stock solution is selected to establish for the test-stock mixture flow characteristics that correspond to flow characteristics of the test liquid before mixing with the stock solution while maintaining in the test-stock mixture the difference in known absorbance characteristics between the first dye and the second dye;
   d. measuring the absorbance values of the first dye and the second dye in the sample solution at a first wavelength and a second wavelength; and
   e. determining the volume of the test-stock mixture aliquot by using the measured absorbance values of the sample solution and the absorbance per pathlength of either or both of the first dye and second dye.

9. The method of claim 8 wherein the liquid holder is a multi-well plate.

10. The method of claim 8 wherein step (e) is performed by using computer-executable software stored on a computer-readable medium, the computer-executable software being capable of calculating volume of the test-stock mixture aliquot based upon absorbance values measured by using the method.

11. The method of claim 8 wherein the liquid holder is in the shape of a truncated cone and wherein the step of determining includes the step of calculating the volume of the aliquot by the equation $$V_S = \frac{\pi \cdot D^2}{4 \cdot a_{\lambda_1}} \cdot (A_{\lambda_1}) + \frac{\pi \cdot D \cdot \tan\theta}{2 \cdot a_{\lambda_1} \cdot a_{\lambda_2}} \cdot (A_{\lambda_1} \cdot A_{\lambda_2}) + \frac{\pi \cdot \tan\theta}{3 \cdot a_{\lambda_1} \cdot a_{\lambda_2}^2} \cdot (A_{\lambda_1} \cdot A_{\lambda_2}^2)$$

where $(V_s)$ is the volume of the aliquot of test-stock mixture, D is the diameter of the liquid holder, $\theta$ is the taper angle of the liquid holder, $(A_{\lambda,1})$ is the measured absorbance of the first dye at the first wavelength, $(A_{\lambda,2})$ is the measured absorbance of the second dye at the second wavelength, $(a_{\lambda,1})$ is the absorbance per unit pathlength of the first dye at the first wavelength, and $(a_{\lambda,2})$ is the absorbance per unit pathlength of the second dye at the second wavelength.

12. The method of claim 8 wherein the liquid holder is in the shape of a truncated square-based pyramid and wherein the step of determining includes the step of calculating the volume of the aliquot by the equation $$V_S = \frac{W_B}{a_{\lambda_1}} \cdot (A_{\lambda_1}) + \frac{W_B \cdot (W_T - W_B)}{h \cdot a_{\lambda_1} \cdot a_{\lambda_2}} \cdot (A_{\lambda_1} \cdot A_{\lambda_2}) + \frac{(W_T - W_B)^2}{3 \cdot h^2 \cdot a_{\lambda_1} \cdot a_{\lambda_2}^2} \cdot (A_{\lambda_1} \cdot A_{\lambda_2}^2)$$

where $(V_s)$ is the volume of the aliquot of test-stock mixture, $(A_{\lambda,1})$ is the measured absorbance of the first dye at the first wavelength, $(A_{\lambda,2})$ is the measured absorbance of the second dye at the second wavelength, $(a_{\lambda,1})$ is the absorbance per unit pathlength of the first dye at the first wavelength, $(a_{\lambda,2})$ is the absorbance per unit pathlength of the second dye at the second wavelength, $(W_B)$ is the width of the bottom of the square well, $(W_T)$ is the width of the top of the square well, and (h) is the height of the entire well.

* * * * *